United States Patent
Berkner et al.

(10) Patent No.: US 11,889,985 B2
(45) Date of Patent: Feb. 6, 2024

(54) ENDOSCOPE HAVING EYEPIECE WITH FIRST AND SECOND PARTS AND ELECTRONIC COMPONENT ARRANGED BETWEEN THE FIRST AND SECOND PARTS

(71) Applicant: OLYMPUS WINTER & IBE GMBH, Hamburg (DE)

(72) Inventors: Sebastian Berkner, Hamburg (DE); Malte Kirsch-Roesner, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 987 days.

(21) Appl. No.: 16/650,983

(22) PCT Filed: Sep. 5, 2018

(86) PCT No.: PCT/EP2018/073900
§ 371 (c)(1),
(2) Date: Jun. 12, 2020

(87) PCT Pub. No.: WO2019/063253
PCT Pub. Date: Apr. 4, 2019

(65) Prior Publication Data
US 2023/0190079 A1    Jun. 22, 2023

(30) Foreign Application Priority Data
Sep. 26, 2017 (DE) .......................... 102017122225.1

(51) Int. Cl.
*A61B 1/00* (2006.01)
*A61B 1/07* (2006.01)

(52) U.S. Cl.
CPC ...... *A61B 1/00121* (2013.01); *A61B 1/00066* (2013.01); *A61B 1/00195* (2013.01); *A61B 1/00197* (2013.01); *A61B 1/07* (2013.01)

(58) Field of Classification Search
CPC ... A61B 1/00121; A61B 1/07; A61B 1/00197; A61B 1/00195; A61B 1/00066
See application file for complete search history.

(56) References Cited

U.S. PATENT DOCUMENTS 4,478,212 A * 10/1984 Asano ................. A61B 1/00124
                                                              396/17
4,736,733 A *  4/1988 Adair ................. A61B 1/00126
                                                              604/533

(Continued)

FOREIGN PATENT DOCUMENTS

DE   10 2015 016 233 A1    6/2017
DE   10 2016 108 095 A1   11/2017

(Continued)

OTHER PUBLICATIONS

Japanese Office Action dated Mar. 2, 2021 received in 2020-537847.

(Continued)

*Primary Examiner* — Anh Tuan T Nguyen
*Assistant Examiner* — Shankar Raj Ghimire
(74) *Attorney, Agent, or Firm* — Scully, Scott, Murphy & Presser, P.C.

(57) ABSTRACT

An endoscope including: a shaft; a main body arranged at a proximal end of the shaft; an eyepiece arranged at a proximal end of the main body; an eyepiece system tube, in which the eyepiece is arranged; an eyepiece cone arranged at a proximal end of the eyepiece, wherein the eyepiece cone comprises at least two parts; and an electronic component arranged between the at least two parts of the eyepiece cone; wherein the electronic component is connected to an electronic circuit arranged inside the endoscope and outside the eyepiece system tube.

8 Claims, 2 Drawing Sheets

(56) References Cited

U.S. PATENT DOCUMENTS

| | | | | |
|---|---|---|---|---|
| 4,779,613 A | * | 10/1988 | Hashiguchi | A61B 1/018 359/512 |
| 4,969,450 A | * | 11/1990 | Chinnock | A61B 1/00195 600/109 |
| 5,243,467 A | * | 9/1993 | Tanaka | G03B 17/08 359/826 |
| 5,569,163 A | * | 10/1996 | Francis | A61B 1/00195 600/162 |
| 5,665,051 A | * | 9/1997 | Quick | A61B 1/00165 600/161 |
| 5,951,463 A | * | 9/1999 | Lombardi | A61B 1/00195 600/172 |
| 6,004,263 A | * | 12/1999 | Nakaichi | A61B 1/0607 600/179 |
| 9,730,718 B2 | * | 8/2017 | Black | A61B 17/29 |
| 10,051,166 B2 | * | 8/2018 | Duckett, III | A61B 1/00105 |
| 10,595,713 B2 | * | 3/2020 | Kiedrowski | A61B 1/00195 |
| 11,278,185 B2 | * | 3/2022 | Berkner | A61B 1/0008 |
| 11,547,280 B2 | * | 1/2023 | Ulmschneider | A61B 1/00128 |
| 2002/0128539 A1 | * | 9/2002 | Higuma | G02B 23/2453 600/162 |
| 2003/0174205 A1 | * | 9/2003 | Amling | A61B 1/042 600/101 |
| 2004/0127768 A1 | * | 7/2004 | Huber | A61B 1/00195 600/162 |
| 2004/0152950 A1 | * | 8/2004 | Kehr | A61B 1/00096 600/163 |
| 2005/0154256 A1 | * | 7/2005 | Breidenthal | A61B 1/00188 600/111 |
| 2006/0069308 A1 | * | 3/2006 | Renner | A61B 1/00195 600/133 |
| 2006/0100483 A1 | * | 5/2006 | Sundet | A61B 1/267 600/156 |
| 2011/0193948 A1 | * | 8/2011 | Amling | A61B 1/00029 348/E7.085 |
| 2011/0282160 A1 | * | 11/2011 | Bhadri | A61B 17/3423 600/236 |
| 2013/0342906 A1 | * | 12/2013 | Dahmen | G02B 23/2476 359/513 |
| 2014/0210977 A1 | | 7/2014 | Amling et al. | |
| 2015/0112133 A1 | * | 4/2015 | Mattes | A61B 1/042 600/109 |
| 2015/0223678 A1 | * | 8/2015 | Goldfain | A61B 3/1208 351/205 |
| 2017/0172701 A1 | * | 6/2017 | Kube | G06K 19/07758 |
| 2017/0319191 A1 | * | 11/2017 | Kiedrowski | A61B 1/00137 |
| 2017/0332885 A1 | * | 11/2017 | Kiedrowski | A61B 1/0011 |
| 2017/0354316 A1 | * | 12/2017 | Mihalca | A61B 1/00126 |
| 2018/0206702 A1 | * | 7/2018 | Liu | G02B 23/2461 |
| 2019/0133432 A1 | * | 5/2019 | Tsai | A61B 1/0684 |
| 2019/0231417 A1 | * | 8/2019 | Sartor | A61L 31/124 |
| 2020/0015661 A1 | * | 1/2020 | Berkner | A61B 1/00128 |
| 2020/0305688 A1 | * | 10/2020 | Sharp | A61B 1/00066 |
| 2020/0305703 A1 | * | 10/2020 | Bala | A61B 1/00105 |

FOREIGN PATENT DOCUMENTS

| | | |
|---|---|---|
| DE | 10 2017 101 681 A1 | 8/2018 |
| EP | 2 428 155 A1 | 3/2012 |
| JP | 2012-55697 A | 3/2012 |
| WO | 2016/081411 A1 | 5/2016 |

OTHER PUBLICATIONS

International Search Report dated Nov. 28, 2018 received in PCT/EP2018/073900.

German Office Action dated Jun. 4, 2018 received in DE 10 2017 122 225.1.

\* cited by examiner

ENDOSCOPE HAVING EYEPIECE WITH FIRST AND SECOND PARTS AND ELECTRONIC COMPONENT ARRANGED BETWEEN THE FIRST AND SECOND PARTS

CROSS-REFERENCE TO RELATED APPLICATION

The present application is based upon and claims the benefit of priority from PCT/EP2018/073900 filed on Sep. 5, 2018, which claims benefit to DE 10 2017 122 225.1 filed on Sep. 26, 2017, the entire contents of each of which are incorporated herein by reference.

BACKGROUND

Field

The present disclosure relates to an endoscope and more particularly to an endoscope having a shaft, a main body arranged at the proximal end of the shaft, an eyepiece arranged at the proximal end of the main body, and an eyepiece cone arranged at the proximal end of the eyepiece.

Prior Art

Endoscopes are often used in medicine and technology to inspect poorly accessible body cavities of a patient or regions of a machine and/or to perform interventions in the corresponding body cavities or regions. While video endoscopes having integrated video cameras are frequently used, endoscopes having an optical image guide, which transmits an image recorded by an objective lens to an eyepiece, at which it can be observed with the naked eye or by means of an external camera, are widespread in particular in medicine. Such endoscopes, often also referred to as optical endoscopes, can be constructed to be narrower and thus more gentle to the patient overall than video endoscopes. Depending on the construction and application of the endoscopes, fiber image guides or lens image guides are used in this case.

Endoscopes generally have an elongated shaft, which can be introduced into the cavity to be inspected. The shaft can be embodied as rigid or flexible, depending on the intended application. A main body is usually provided at the proximal end of the shaft. The main body is used for handling the endoscope and can moreover contain fittings, through which liquids and/or instruments can be introduced or removed.

The eyepiece is generally arranged at the proximal end of the main body and ends in an eyepiece cone. The eyepiece cone was originally used for the comfortable contact of the eye of a user, but presently is usually used to place an external camera on the endoscope.

In the course of the refinement of endoscopes, diverse technologies have been developed in particular for video endoscopes, which contain electronic components. However, these are hardly integrated into optical endoscopes, since the latter do not have any electrical contact to the outside as such and therefore cannot be supplied with electrical energy. Recently, however, possibilities have been developed for transmitting electrical energy and signals wirelessly to endoscopes.

Arranging electronic components for the transmission in the eyepiece cone suggests itself for the wireless transmission of energy and/or signals in this case, since these components can thus be placed close to externally supplied assemblies, for example, a camera. However, a satisfactory technical solution has not yet been found for the arrangement of such components in the eyepiece cone.

SUMMARY

An object is therefore to provide a possibility for integrating an electronic component into the eyepiece cone of an endoscope.

Such object can be achieved by an endoscope having a shaft, a main body arranged at the proximal end of the shaft, an eyepiece arranged at the proximal end of the main body, and an eyepiece cone arranged at the proximal end of the eyepiece, where the eyepiece cone comprises at least two parts, between which an electronic component is arranged.

Due to the two-part construction of the eyepiece cone, the electronic component can be integrated easily into the endoscope, without the fundamental structure of the endoscope having to be modified.

In one embodiment of an endoscope, the parts of the eyepiece cone can be embodied as movable in relation to one another at least during the assembly of the endoscope. This enables a simple assembly of the endoscope, wherein firstly the electronic component is introduced between the parts of the eyepiece cone, and these parts are subsequently moved in relation to one another into the final position thereof. In this case, the parts of the eyepiece cone can be connected to one another during or after the assembly of the endoscope in such a way that a movement of the parts in relation to one another is no longer possible. Thus, a joining gap between the parts of the eyepiece cone can be closed after the joining together by adhesive bonding, soldering, or welding, to prevent the penetration of moisture, dirt, or germs into the eyepiece cone.

In an embodiment, the endoscope can comprise an eyepiece system tube, in which the eyepiece is arranged, and the electronic component is connected to an electronic circuit, which is arranged inside the endoscope and outside the eyepiece system tube.

In an embodiment of an endoscope, a first part of the eyepiece cone can be screwed together with a thread provided on the eyepiece system tube. Such a screw connection is simple and reliable to produce.

The eyepiece system tube of an endoscope can protrude in portions into the main body, and a sleeve can be arranged around the portion of the eyepiece system tube not protruding into the main body. Such a sleeve is often used for the purpose of attaching identifiers to the endoscope and is therefore also referred to as an inscription sleeve. In parallel or alternatively, the sleeve can be used to ensure a predetermined geometrical external shape of the endoscope, while the location of the eyepiece system tube can be changed during an optical adjustment of the endoscope.

A second part of the eyepiece cone of an endoscope according to one embodiment can be screwed together with a thread provided on the sleeve.

In an embodiment of an endoscope, the connection between the electronic component and the electronic circuit can be established via a connecting element, which is arranged on the outer side of the eyepiece system tube. In this way, it is possible to arrange the electronic circuit in the endoscope and connect it to the connecting element during a first assembly step of the endoscope, and to connect the electronic component to the connecting element in a second assembly step, so that the electronic component and the electronic circuit are connected via the connecting element. The connecting element can comprise solder pads, screw connectors, and/or plug connectors.

The sleeve can comprise a passage window in the region of the connecting element. Terminal wires of the electronic element can be led through the passage window. The passage window can be arranged in the fully assembled state of the sleeve in such a way that the terminal wires are connected to the connecting element through the passage window.

In one embodiment, the passage window can be covered in the assembled state of the endoscope by a part of the eyepiece cone, such as the second part. An additional closure element is thus not required for the passage window.

The electronic component can comprise a coil. The electronic circuit can comprise an electrical consumer, for example, a light source and/or a window heater and/or an actuator and/or a video chip.

BRIEF DESCRIPTION OF THE DRAWINGS

The embodiments are explained in greater detail hereafter on the basis of several exemplary illustrations. In the figures.

DETAILED DESCRIPTION

Figure 1:
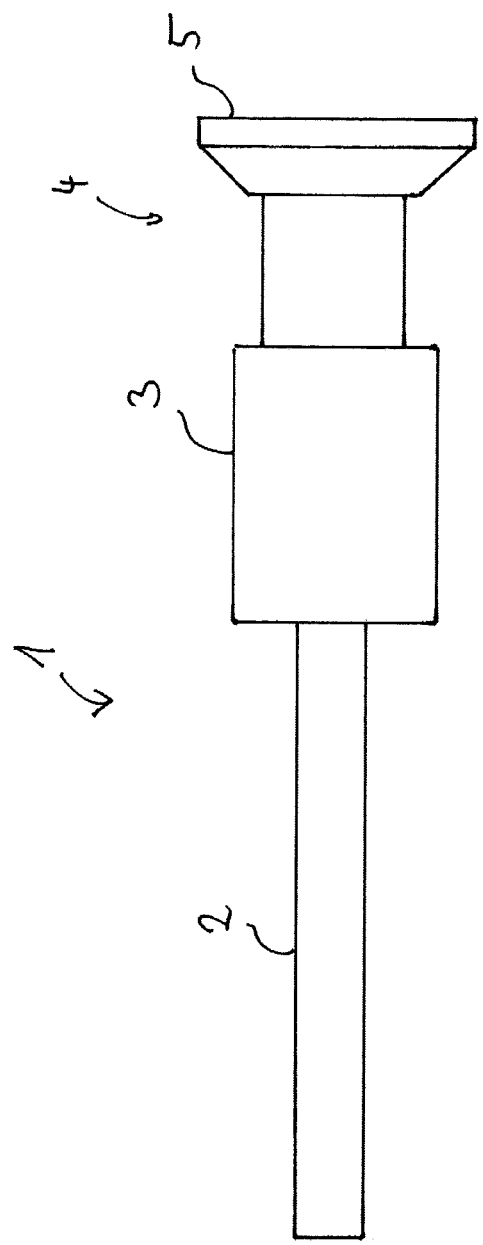
FIG. 1 illustrates an endoscope.

An endoscope 1 is shown in FIG. 1. The endoscope 1 comprises a shaft 2 and a main body 3. Furthermore, the endoscope 1 comprises an eyepiece 4, arranged at the proximal end of the main body, having an eyepiece cone 5.

Figure 2:
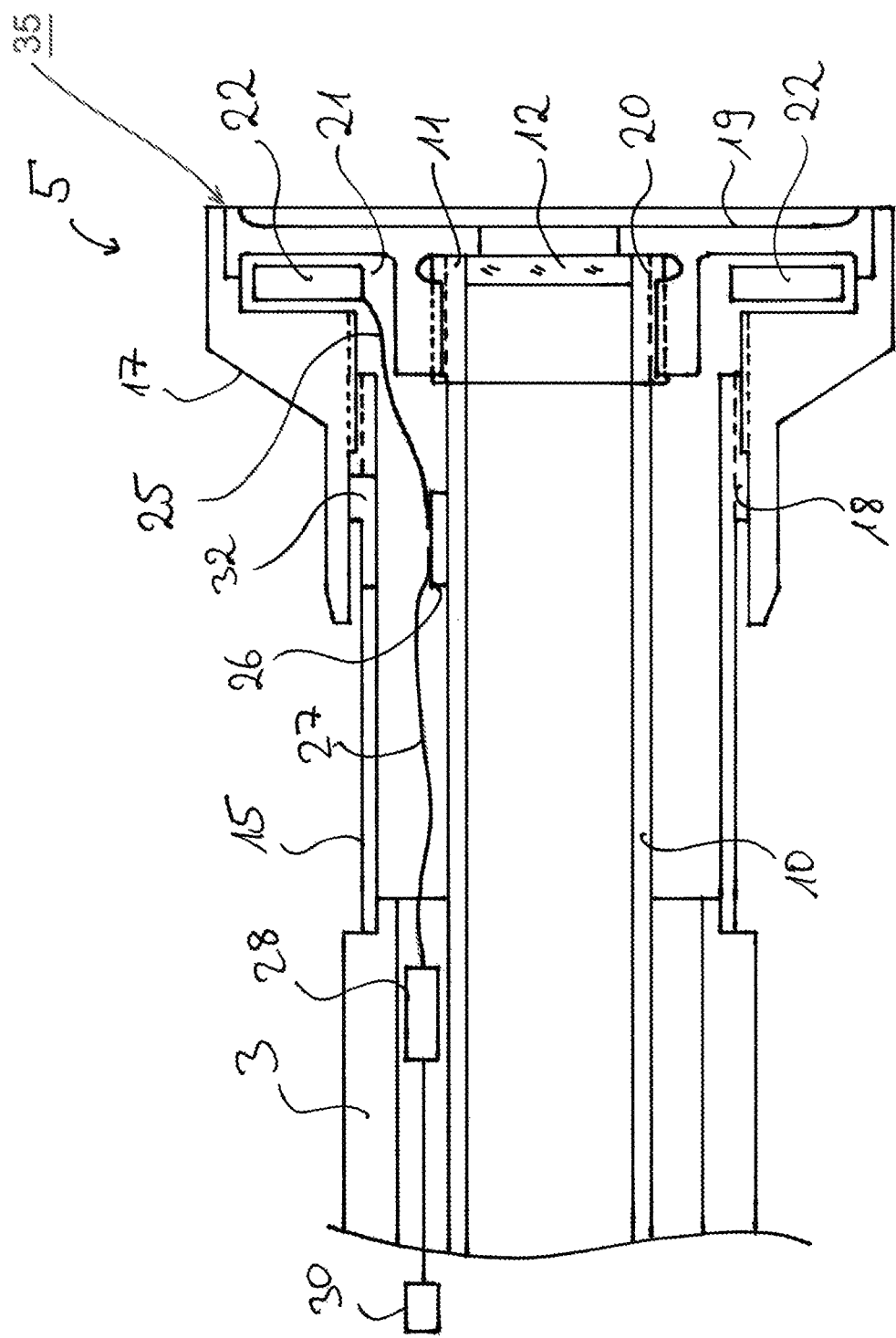
FIG. 2 illustrates the proximal portion of an endoscope in a simplified sectional view.

The proximal end of the endoscope 1 is shown in detail in FIG. 2. An eyepiece system tube 10 protrudes proximally out of the main body 3. Optical components of the eyepiece 4, which are not shown for the sake of clarity, are arranged in the eyepiece system tube 10. The eyepiece system tube 10 ends in an eyepiece window frame 11, in which an eyepiece window 12 is inserted in a sealed manner, for example, by adhesive bonding or soldering.

To avoid thermal tensions during the soldering of the eyepiece window 12, which usually consists of sapphire, into the eyepiece window frame 11, the eyepiece window frame can consist of a material, the coefficient of thermal expansion of which approximately corresponds to that of the eyepiece window 12. A steel of the type Sandvik 1.4523, for example, comes into consideration for this purpose.

For the optical adjustment of the endoscope 1, it can be necessary to displace the eyepiece system tube 10 having the optical components located therein in relation to the main body 3 during the production or maintenance and fix it in the correct position. So as not to change the external contour of the endoscope 1 at the same time, a sleeve 15, which encloses the eyepiece system tube 10, is fastened on the main body 3.

The endoscope is proximally terminated by the eyepiece cone 5, which is constructed from two parts. A first, outer part 17 is screwed onto a thread 18 arranged at the proximal end of the sleeve 15. A second, inner part 19 is screwed onto a thread 20 arranged on the proximal end of the eyepiece window frame 11. A cavity 21, in which an electronic component 22, in the present case a coil, finds space, remains between the parts 17 and 19.

Feed lines 25 of the electronic component 22 are connected via a connecting element 26 to lines 27 of an electronic circuit 28. The electronic circuit 28 can be used to process a signal captured via the electronic component 22, for example, to convert an AC voltage signal received via a coil into a supply voltage for electrical consumers 30 arranged in the endoscope 1. The consumer 30 can be, inter alia, an electrical light source, a window heater, an actuator, and/or a video chip.

Reference is expressly made to the corresponding embodiments in the patent application DE102016108095 (PO-2016-008 DE) of the applicant with respect to possible embodiments and arrangements of the electronic component 22, the electronic circuit 28, and the consumers 30.

The connecting element 26 is fastened on the outer side of the eyepiece system tube 10 and can comprise one or more solder pads or screw clamps.

During the assembly of the endoscope 1, firstly the eyepiece system tube 10 is introduced into the main body 3, adjusted, and then fixed. The lines 27 of the electronic circuit 28 are then fastened on the connecting element 26. The sleeve 15 is subsequently placed on the main body 3 and fixed, for example by pressing. In this case, seal elements (not shown here for reasons of clarity) can be introduced between the main body 3 and the sleeve 15.

The sleeve 15 is aligned during the assembly so that an assembly window 32 arranged in the wall of the sleeve 15 is placed over the connecting element 26.

In a next step, the outer part 17 of the eyepiece cone 5 is screwed onto the sleeve 15 and firstly moved far enough in the distal direction that the assembly window 32 is proximally accessible.

Subsequently, the electronic component 22 is placed onto the inner part 19 of the eyepiece cone 5 and the latter is screwed onto the thread 20 of the eyepiece window frame 11. In this case, the feed lines 25 are aligned in the direction of the sleeve 15. If the inner part 19 is fixedly screwed together with the eyepiece window frame 11, the electronic component 22 is aligned so that its feed lines 25 extend into the region of the connecting element, this is observed through the assembly window 32.

The feed lines 25 are now connected, for example, soldered, to the connecting element 26 by means of tools grasping or acting through the assembly window 32.

Next, the outer part 17 of the eyepiece cone is again screwed in the proximal direction, so that it conceals the assembly window 32. In this case, the proximal edges of the parts 17, 19 are aligned in a planar manner in relation to one another, so that the eyepiece cone 5 has a flat proximal end face. A ring gap 35 remaining between the parts 17, 19 can be closed leak-tight by means of an adhesive, to prevent the penetration of contaminants into the ring gap 35.

Further seal elements, for example, O-rings, can be arranged between the outer part 17 of the eyepiece cone and the sleeve 15 to also prevent the penetration of contaminants here.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An endoscope comprising:
a shaft;
a main body arranged at a proximal end of the shaft;
an eyepiece arranged at a proximal end of the main body, the eyepiece having an eyepiece window configured for viewing by a human eye or an external camera removably connected to the eyepiece;

an eyepiece system tube, in which the eyepiece is arranged, the eyepiece system tube extending distally from the eyepiece;

an eyepiece cone arranged at a proximal end of the eyepiece, wherein the eyepiece cone comprises at least a first part and a second part; and an electronic component arranged in a cavity formed between the at least first part and second part of the eyepiece cone;

wherein the electronic component is connected to an electronic circuit arranged inside the endoscope and outside the eyepiece system tube;

the eyepiece system tube having a first portion protruding distally into the main body in a longitudinal direction of the main body and a second portion exposed proximally from the main body in the longitudinal direction of the main body, the endoscope further comprising a sleeve arranged around the second portion of the eyepiece system tube;

the second part of the eyepiece cone includes a first threaded portion arranged on a first circumferential surface of the second part, the first threaded portion being in mating engagement with a second threaded portion arranged on a second circumferential surface of the sleeve; and the connection between the electronic component and the electronic circuit is established via a connecting element arranged on an outer circumferential surface of the eyepiece system tube.

2. The endoscope as claimed in claim 1, wherein the at least first part and second part of the eyepiece cone are configured to be movable in relation to one another at least during assembly of the endoscope.

3. The endoscope as claimed in claim 1, wherein the first part of the eyepiece cone includes a third threaded portion arranged on a third circumferential surface of the first part, the third threaded portion being in mating engagement with a fourth threaded portion provided on the eyepiece system tube, the fourth threaded portion being arranged on a fourth circumferential surface of the eyepiece system tube.

4. The endoscope as claimed in claim 1, wherein the sleeve comprises a passage window formed in a wall of the sleeve, the passage window corresponding to a longitudinal position of the connecting element.

5. The endoscope as claimed in claim 4, wherein the passage window is configured to be covered by one of the at least first part and second part of the eyepiece cone in an assembled state of the endoscope.

6. The endoscope as claimed in claim 1, wherein the electronic component comprises a coil.

7. The endoscope as claimed in claim 1, wherein the electronic circuit comprises an electrical consumer.

8. The endoscope as claimed in claim 7, wherein the electrical consumer is selected from a group consisting of a light source, a window heater, an actuator and a video chip.

* * * * *